United States Patent
Choi et al.

(10) Patent No.: US 8,411,366 B2
(45) Date of Patent: Apr. 2, 2013

(54) OPTICAL PROBE AND OPTICAL SYSTEM THEREFOR

(75) Inventors: Min-Seog Choi, Seoul (KR); Seung-Wan Lee, Suwon-si (KR); Woon-Bae Kim, Seoul (KR); Seung-Tae Choi, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 42 days.

(21) Appl. No.: 13/101,192

(22) Filed: May 5, 2011

(65) Prior Publication Data

US 2012/0127724 A1 May 24, 2012

(30) Foreign Application Priority Data

Nov. 19, 2010 (KR) .................... 10-2010-0115869

(51) Int. Cl.
*G02B 27/30* (2006.01)
*G02B 26/08* (2006.01)
*G02B 1/06* (2006.01)

(52) U.S. Cl. .................. 359/641; 359/197.1; 359/666

(58) Field of Classification Search .......... 359/641, 359/197.1, 212.1, 223.1, 224.1, 224.2, 230, 359/290–297, 666
See application file for complete search history.

(56) References Cited

U.S. PATENT DOCUMENTS

| | | | | |
|---|---|---|---|---|
| 5,315,375 | A * | 5/1994 | Allen | 356/417 |
| 5,321,501 | A | 6/1994 | Swanson et al. | |
| 5,386,427 | A * | 1/1995 | Zayhowski | 372/34 |
| 6,134,003 | A | 10/2000 | Tearney et al. | |
| 6,485,413 | B1 | 11/2002 | Boppart et al. | |
| 2006/0245084 | A1 * | 11/2006 | Brustle et al. | 359/744 |
| 2007/0035855 | A1 | 2/2007 | Dickensheets | |
| 2007/0223898 | A1 * | 9/2007 | Purwanto | 396/17 |
| 2008/0192139 | A1 * | 8/2008 | Kanai et al. | 348/360 |
| 2009/0086314 | A1 * | 4/2009 | Namba et al. | 359/383 |
| 2009/0147373 | A1 | 6/2009 | Rolland et al. | |
| 2009/0323076 | A1 * | 12/2009 | Li et al. | 356/479 |

FOREIGN PATENT DOCUMENTS

KR 10-1999-002601 A 1/1999

* cited by examiner

*Primary Examiner* — Dawayne A Pinkney
(74) *Attorney, Agent, or Firm* — Sughrue Mion, PLLC

(57) ABSTRACT

An optical probe and an optical system therefor are provided. The optical probe is includes a housing configured to house the optical system and the housing has a transparent window therein. the optical system includes a light emitting unit, a collimation lens, and a focusing lens. A numerical aperture of the optical system is adjustable by adjusting a pupil diameter of the collimation lens and a focal length of the focusing lens. The pupil diameter of the collimation lens is adjustable based on a variable focal lens or by adjusting a distance between the collimation lens and the light emitting unit.

20 Claims, 10 Drawing Sheets

OPTICAL PROBE AND OPTICAL SYSTEM THEREFOR

CROSS-REFERENCE TO RELATED APPLICATION

This application claims priority under 35 U.S.C. §119(a) of Korean Patent Application No. 10-2010-0115869, filed on Nov. 19, 2010, in the Korean Intellectual Property Office, the entire disclosure of which is incorporated herein by reference

BACKGROUND

1. Field

The following description relates to an optical apparatus, and more particularly, to an optical probe which is inserted into a tube to pick up an image.

2. Description of the Related Art

In the field of medical imaging, a need for tomography to obtain an image of an inner portion of tissue surface with a high resolution along with information on blood vessels or tissue surface of internal organs is increasing. Specifically, since most cancer cells start from epithelial cells and spread to the inside of dermal cells in which blood vessels are located, cancer cells of very small size (50~100 μm) in the early stage need to be detected in the epithelial cells to drastically reduce damage from the cancer, and to this end, a high-resolution tomography apparatus is required.

Typical magnetic resonance imaging (MRI) or computerized tomography (CT), and supersonic wave imaging may obtain a cross-sectional image of an organ through the use of waves that penetrate the skin. However, these techniques generate an output with a low resolution and thus are of limited use in detecting the early-stage, small cancer cells. In addition, optical coherence tomography (OCT) which has been recently implemented employs light that penetrates less deeply, i.e., only about 2~3 mm, into the skin, compared to the other existing imaging techniques. OCT, however, has a resolution ten times higher than that of the other imaging techniques, and thus can provide an enhanced probability of detection of early-staged cancer. However, since OCT techniques result in resolutions lower than that of a microscope, it cannot be a substitute for biopsy or histology for determining the presence or existence of real cancer cells.

Optical probes are inserted into tube-shaped internal organs such as blood vessels and obtain cross-sectional images of tissues or of inner sides of the organs. The optical probes may be used for other purposes, such as non-destructive internal instruction, in addition to medical purposes. An optical probe includes an optical system therein, and optical systems for use to obtain images to substitute for biopsies or histologies are required to have a relatively low depth of field (DOF), and a relatively high horizontal resolution. Further, like other imaging apparatuses, optical probes should be capable of picking up cross-sectional images of deep inside tissues with a high depth of field. However, the depth of field is in inverse proportion to a horizontal resolution, and an optical system with low numerical aperture (NA) is required to increase the depth of field as in OCT whereas an optical system with high NA is required to acquire high horizontal resolution.

SUMMARY

The following description relates to an optical probe and an optical system for the optical probe which has a large depth of field allowing tomography of deeper portions of tissue and which is capable of obtaining a high-resolution image of an area close to a tissue surface.

In addition, the following description relates to an optical probe and an optical system having a variable numerical aperture, such that changes in a depth of focus and/or a resolution may be maximized.

According to an aspect of an exemplary embodiment, there is provided an optical system including: a light emitting unit comprising a light source; a collimation lens which collimates the light emitted from the light emitting unit; a pupil diameter adjusting means for adjusting a pupil diameter of the collimation lens; and a focusing lens which focuses the light transmitted from the collimation lens onto an object, wherein a focal length of the focusing lens is variable.

According to an aspect of another exemplary embodiment, there is provided an optical probe including: a housing comprising at least one side wall and a transparent window in the at least one sidewall; and an optical system disposed within the housing. The optical system comprises a collimation lens and a focusing lens, wherein a pupil diameter of the collimation lens is adjustable and a focal length of the focusing lens is adjustable, and thereby, a numerical aperture of the optical system is adjustable.

Other features and aspects may be apparent from the following detailed description, the drawings, and the claims.

BRIEF DESCRIPTION OF THE DRAWINGS

The above and/or other aspects will become apparent and more readily appreciated from the following description of embodiments, taken in conjunction with the accompanying drawings, in which.

DETAILED DESCRIPTION

Figure 1:
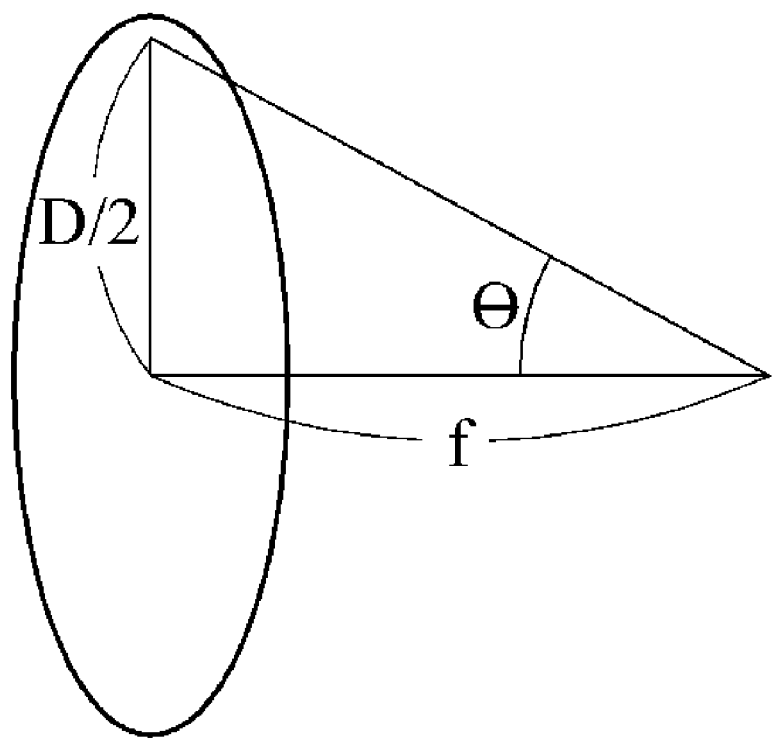
FIG. 1 is a diagram illustrating a lens for explaining a definition of a NA.

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness. It will also be understood that when a first layer is referred to as being "on" a second layer, it can be directly on the second layer, or intervening layers may also be present.

Elements, features, and structures are denoted by the same reference numerals throughout the drawings and the detailed description, and the size and proportions of some elements may be exaggerated in the drawings for clarity and convenience.

FIG. 1 illustrates a lens for explaining a definition of NA. An NA of an optical system is a dimensionless number that specifies the range of angles over which the optical system can accept or emit light. The definite definition of NA may differ among various fields of optics, and in an optical system such as an object lens, the NA of a lens may be defined as Equation 1 below.

$$NA = n\sin\theta = \frac{D}{\sqrt{4f^2 + D^2}},$$

where n denotes the index of refraction of the lens is working, θ is a half-angle of a maximum cone of light picked up by the lens. In addition, D denotes the pupil diameter of the lens, and f denotes the focal length of the lens.

Referring to Equation 1, to change the NA of an optical system, the focal length f and the pupil diameter D of the system must be adjusted. In this case, if either the focal length f of the optical system or the pupil diameter is adjusted, change in NA is relatively small. To increase the change in the NA, it is more effective to adjust both the focal length f and the pupil diameter D of the optical system. In addition, by increasing the change of the NA, an image with a relatively large depth of field and a relatively high horizontal resolution may be acquired.

Figure 2A:
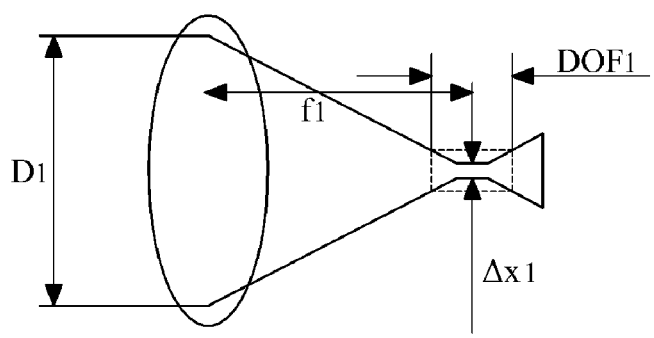
FIG. 2A is a diagram illustrating a lens for explaining a relationship between a depth of field and a resolution when NA is large.
Figure 2B:
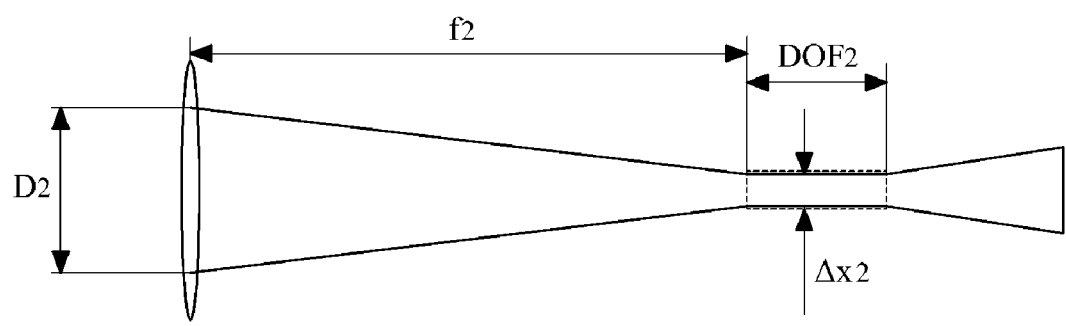
FIG. 2B is a diagram illustrating a lens for explaining a relationship between a depth of field and a resolution when NA is small.

FIGS. 2A and 2B illustrate lenses for explaining a relationship between NA, DOF, and resolution. Referring to FIG. 2A, to obtain a high horizontal resolution such as that of a microscope, a focal diameter Δx1 is to be minimized. In this case, the depth of field DOF1 is shortened. Then, as the focal diameter Δx1 decreases, the NA increases, and thus, an NA of, for example, about more than 0.5 is obtained. In addition, to obtain larger focal diameters Δx1, the focal length f should be as short as possible, and the pupil diameter D1 should be as large as possible.

In contrast, referring to the example illustrated in FIG. 2B, tomography systems such as OCT used to acquire images of deeper portions of a sample are required to have a deep depth of field DOF2. In this case, the focal diameter Δx2 is increased. Moreover, when the depth of field DOF2 is deeper, the NA should be small, and thus, the NA should be smaller than, for example, about 0.2. To acquire a smaller NA, the focal length f2 should be as long as possible, and the pupil diameter D2 should be as small as possible.

Figure 3:
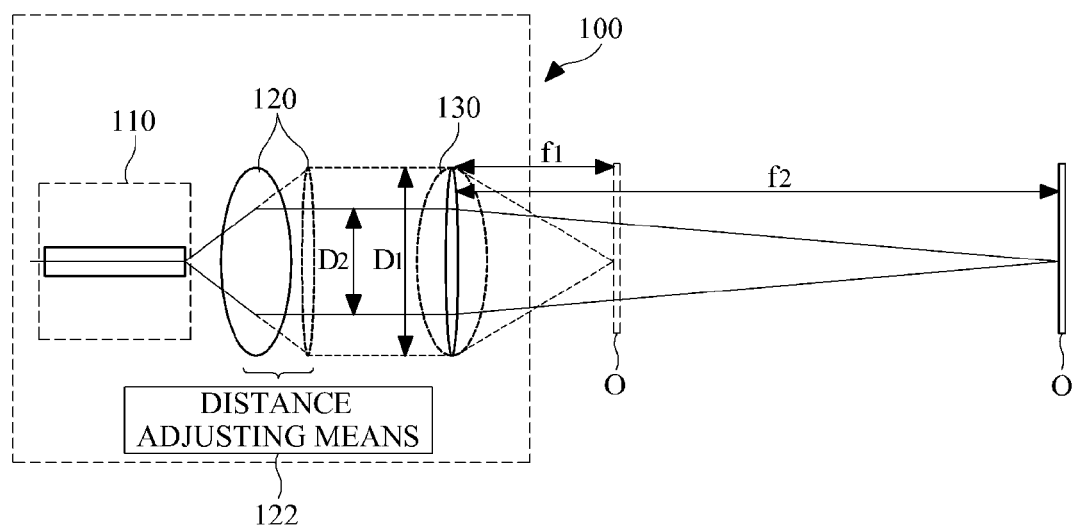
FIG. 3 is a diagram illustrating a structure of an optical system for an optical probe according to an embodiment.

FIG. 3 illustrates a structure of an optical system for an optical probe according to an embodiment. The optical probe may be used in tube-shaped blood vessels such as arteries, or other organs, for example, the esophagus and the intestines. However, it will be understood by those skilled in the art that the optical probe is applicable to other non-biological fields. The described optical system may be mounted in a housing having a cylindrical shape. In such a case, elements constituting the optical system may be directly or indirectly fixed to the housing, and some elements may be horizontally or vertically movably or rotatably connected to the housing.

Referring to the example illustrated in FIG. 3, an optical system 100 for n optical probe may include a light emitting unit 110, a collimation lens 120, and a focusing lens 130. The optical system 100 may further include a distance adjusting means 122 between the light emitting unit 110 and the collimation lens 120.

The light emitting unit 110 emits light toward the collimation lens 120, wherein the light is emitted from a light source at a predefined distance from the collimation lens 120. The light source may vary in its type, and the light may be transferred to the light emitting unit 110 through an optical fiber extending from the light source. The light emitting unit 110 may function effectively as a point light source that emits light toward the lens 120 of the optical system 100. Unlike other optical systems, the optical system described herein for use in an optical probe may have a light source with a very small diameter, and optical fibers suitable to use with such an optical system. The light emitted from an end of the light emitting unit 110 may be emitted toward the collimation lens 120 over a predefined angle of emission.

Then, the collimation lens 120 may collimate the light emitted from the light emitting unit 110, and transmit the collimated light to a focusing lens 130. The collimated light transmitted to the focusing lens 130 has a predefined diameter D1 or D2, which corresponds to a pupil diameter of the collimation lens 120. The collimation lens 120 may be a single lens or a group of lenses.

The optical system 100 may include a pupil diameter adjusting means to adjust the pupil diameter. The pupil diameter of the collimation lens 120 may be adjusted in various ways, and FIG. 3 shows one example of an adjustment method. More specifically, the optical system 100 may include the collimation lens 120 having a variable focal lens and a distance adjusting means for changing a distance from the collimation lens 120 to the light emitting unit 110 in order to adjust the pupil diameter.

The distance adjusting means 122 may vary in its type, and, for example, a mechanical device such as a micro motor or micro actuator which is used for a mobile device may be employed as a driving device. In addition, the collimation lens 120 which includes a variable focal lens should be a type of lens applicable to an optical system used in a compact optical device such as an optical probe. For example, the variable focal lens may be a shape-changeable lens. One example of such shape-changeable variable focal lens may be a liquid lens driven by a polymer actuator. An exemplary liquid lens is disclosed in U.S. patent application Ser. Nos. 12/787,787, titled "FLUIDIC LENS AND METHOD OF MANUFACTURING THE SAME," filed on May 26, 2010, 12/784,625, titled "LIQUID LENS," filed on May 21, 2010, and 13/035,072, titled "FLUIDIC LENS," filed on Feb. 25, 2011, by the same applicant as the present invention. A liquid lens driven by a polymer actuator may obtain a relatively large displacement even at a low driving voltage, and have a fast driving speed.

The focusing lens 130 may emit the collimated light transmitted from the collimation lens 120 to an object O. The focusing lens 130 may be formed of a single lens or a plurality of lens groups, and a variable focal lens may be used as the focusing lens 130 or may be included in the lens groups. For example, like the above-described collimation lens 120, the focusing lens 130 may include a shape-changeable variable focal lens such as a liquid lens driven by a polymer actuator. In addition, the optical system 100 may further include a location changing means (not illustrated) to change a location of the focusing lens 130. The location changing means may be, for example, the same device as the distance adjusting means 122 described above. The location changing means may assist in accurately locating a focal point on the object O when it is difficult to move or change the location of the optical system 100.

As such, the optical system 100 for an optical probe may use a variable focal lens as the collimation lens 120, or include the distance adjusting means 122 between the collimation lens 120 and the light emitting unit 110 to adjust the distance therebetween, so that the pupil diameter of the collimation lens 120 can be adjusted to D1, D2 or any value between D1 and D2. In addition, the optical system 100 may use a variable focal lens as the focusing lens 130 to adjust a focal length to f1, f2, or any value between f1 and f2. Thus, the optical system 100 may change one or both of the pupil diameter D and the focal length f, thereby adjusting the NA to be suitable to various purposes.

In particular, the optical system 100 for an optical probe may provide a relatively high horizontal resolution and a relatively deep depth of field. For example, in a case such as detection of early-stage cancer cells which requires a depth of field which is not significantly deep but a relatively high horizontal resolution, the optical system 100 may be manipulated to have a large pupil diameter and a short focal length such that the NA becomes equal to or more than, for example, 0.5. Then, in a case such as tomography for deep tissue image which requires a relatively low horizontal resolution but a deep depth of field, the optical system 100 may be manipulated to have a small pupil diameter and a long focal length such that the NA becomes equal to or less than 0.2.

Figure 4:
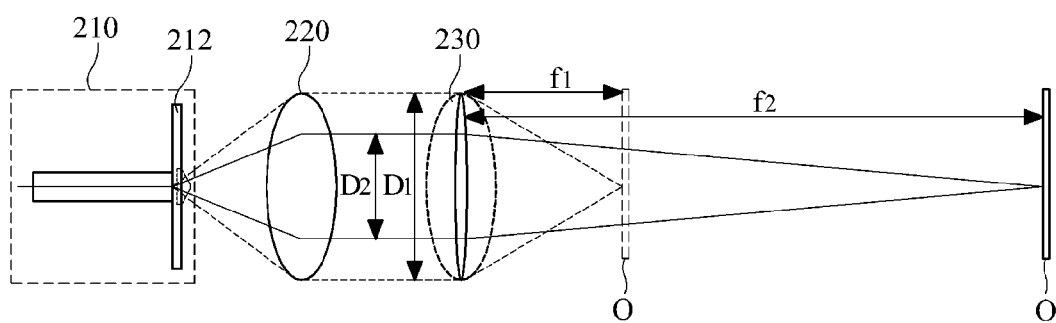
FIG. 4 is a diagram illustrating a structure of the optical system for an optical probe according to an embodiment.

FIG. 4 illustrates a structure of the optical system for an optical probe according to another embodiment. Referring to FIG. 4, the optical system 200 may include a light emitting unit 210, a collimation lens 220, and a focusing lens 230. The collimation lens 220 may be disposed at an end of the light emitting unit 210, and the light emitting unit 210 may include a variable focal lens 212 that is capable of changing an angle of emission of the emitted light. The optical system 200 may differ from the optical system 100 shown in FIG. 3 in that the variable focal lens 212 is provided at one end of the light emitting unit 210 as a means of adjusting the pupil diameter of the collimation lens 220. In addition, although a distance between the light emitting unit 210 and the collimation lens 220 may be fixed since the collimation lens 220 of the optical system 200 may be fixed to a housing (not illustrated) or the like, the distance may vary among different embodiments. Hereinafter, the optical system 200 will be described, focusing on the difference from the optical system 100 shown in FIG. 3.

The light emitting unit 210 may be used to emit light toward the collimation lens 220, wherein the light is transmitted from a light source provided at a predefined distance from the collimation lens 220. A variable focal lens 212 may be disposed at an end of the light emitting unit 210, and may be of various types. For example, a liquid lens driven by a polymer actuator which is a variable focal lens changeable in shape may be used as the variable focal lens 212. The variable focal lens 212 may adjust an angle of emission of the light emitted from the end of the light emitting unit 210 to the collimation lens in order to adjust a pupil diameter of the collimation lens 220.

Figure 5A:
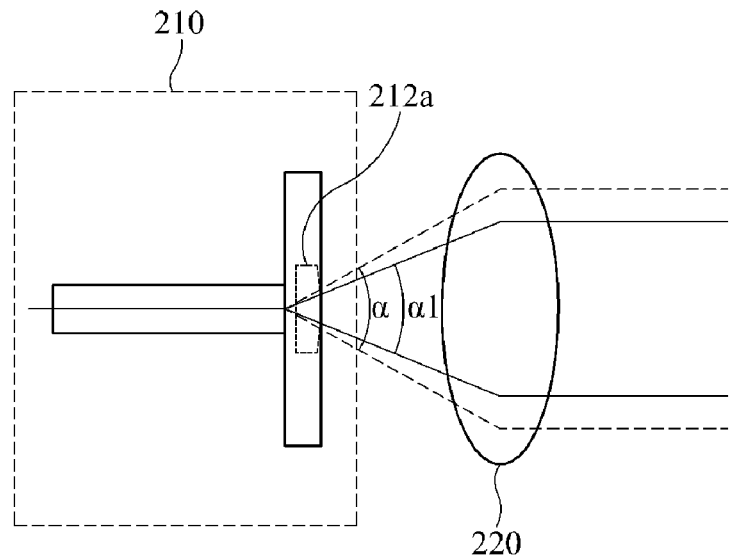
FIG. 5A is a diagram illustrating a shape of a variable focal lens included in the light emitting unit of the optical system illustrated in FIG. 4.
Figure 5B:
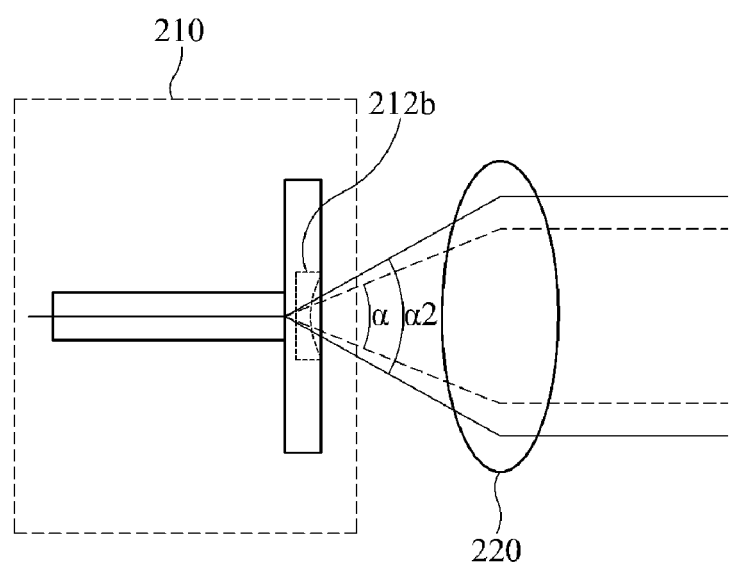
FIG. 5B is a diagram illustrating another shape of a variable focal lens included in the light emitting unit of the optical system illustrated in FIG. 4.

FIGS. 5A and 5B illustrate examples of adjusting an angle of the light emitted from the light emitting unit using variable focal lenses 212a and 212b. Referring to FIG. 5A, the variable focal lens 212a has a convex surface facing the collimation lens 220. Thus, the angle of light emitted from the light source over a predefined angle α may be decreased (α1<α) by refraction while passing through the variable focal lens 212, and as a result, a pupil diameter of the collimation lens 110 becomes smaller. In contrast, referring to FIG. 5B, the variable focal lens 212b has a concave surface facing the collimation lens 220. Hence, the angle of the light emitted from the light source over a predefined angle α may be decreased (α2>α) by refraction while passing through the variable focal lens 212, and as a result, the pupil diameter of the collimation lens 220 increases.

In addition, the collimation lens 220 may collimate the light emitted from the light emitting unit 210 and transmit the collimated light to the focusing lens 230. According to this embodiment, the pupil diameter adjusting means of the collimation lens 220 is included in the light emitting unit 210, and thus the collimation lens 220 may be fixed in its location. Also, the collimated light transmitted from the collimation lens 220 to the focusing lens 230 may have a predefined diameter D1 or D2, and the diameter D1 or D2 may be varied with the angle of the light emitted from the light emitting unit 210, and thus the collimation lens 220 may not be necessarily a variable focal lens.

The focusing lens 230 may emit the collimated light transmitted from the collimation lens 220 to an object O. A variable focal lens may be used as the focusing lens 230 to adjust a focal length. For example, like the collimation lens 120 shown in FIG. 3, the focusing lens 230 may be a variable focal lens which is a shape-changeable lens, such as a liquid lens driven by a polymer actuator. Moreover, the optical system 200 for used in an optical probe may further include a location changing means (not illustrated) that is capable of changing a location of the focusing lens 230.

As such, the optical system 200 may include a variable focal liquid lens 212 disposed at an end of the light emitting unit 210 to adjust a pupil diameter of the collimation lens 220 to D1, D2, or any value between D1 and D2. Additionally, a variable focal lens is used as the focusing lens 230 to adjust the focal length to f1, f2, or any value between f1 and f2. Hence, the optical system 200 may have a pupil diameter D and a focal length f which are both adjustable, thereby enabling an adjustment of the NA to be suitable for various purposes.

The optical systems 100 and 200 described with reference to FIGS. 3 and 4 may be used for an optical probe having a front view. The optical probe having a front view may include a tube-shaped housing (not illustrated) which has the optical system 100 or 200 mounted therein and a transparent window installed on a distal end of the housing. In this case, the distal end is determined based on a location of a light emitting unit. Thus, light which is to be focused in front of the focusing lenses 130 and 230 of the respective optical systems 100 and 200 may travel straight and reach the object O via the transparent window. Then, light reflected from the object O may travel straight through the transparent window and reach the optical systems 100 and 200. To this end, each of the light emitting units 110 and 210 may include an image sensor to receive light reflected from the object O. In addition, as described above, elements constituting each of the optical systems 100 and 200 may be fixed directly or indirectly to the housing, and some elements may be horizontally or vertically movably or rotatably fixed to the housing.

The optical probe having a forward view may further include a scanning apparatus to change a location to be imaged. The scanning apparatus may change a location at which the light from each of the focusing lenses 130 and 230 is focused, thereby changing the imaging location without moving the optical probe. In this example, the scanning apparatus may be one of various types, and may be, for example, a scanning apparatus disclosed in U.S. Pat. No. 5,321,501 or U.S. Pat. No. 6,485,413, which are incorporated herein by reference.

Figure 6A:
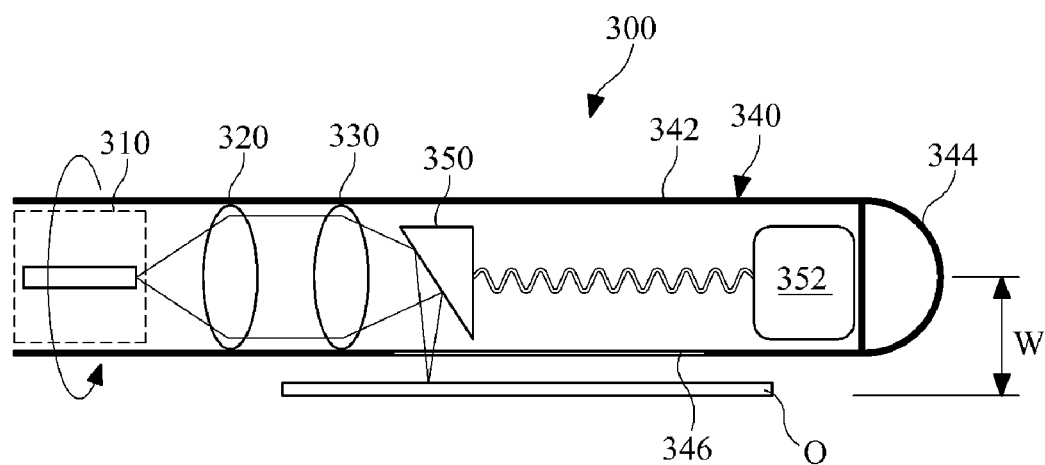
FIG. 6A is a diagram illustrating an optical probe in a given status according to an embodiment.
Figure 6B:
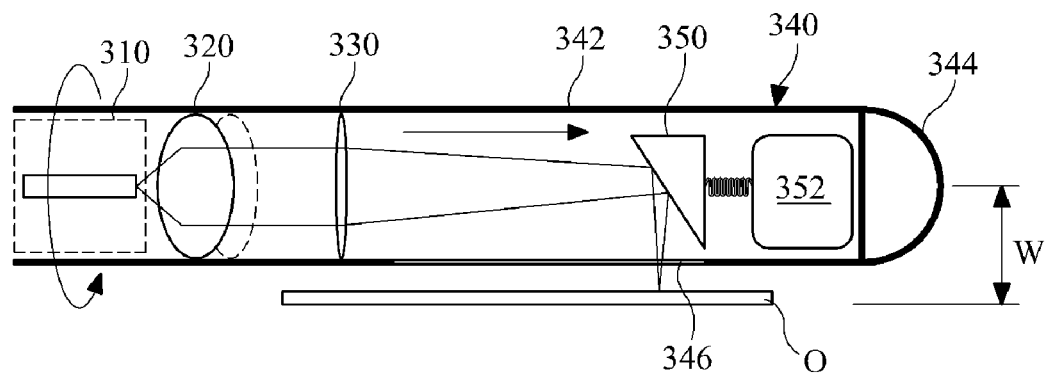
FIG. 6B is a diagram illustrating the optical probe in another given status according to an embodiment.

FIGS. 6A and 6B illustrate a structure of an optical probe according to an embodiment. In the example illustrated in FIG. 6A, the NA of an optical system of the optical probe 300 is relatively large, and in the example illustrated in FIG. 6B, the NA is relatively small. The optical system shown in FIGS. 6A and 6B may have a structure substantially similar to the structure of the optical system 100 shown in the example illustrated in FIG. 3. The optical system of the optical probe 300 shown in the examples illustrated in FIGS. 6A and 6B is characterized in that as a pupil diameter adjusting means, a collimation lens 320 is a variable focal lens and a distance adjusting means (not illustrated) is disposed to adjust a distance between a light emitting unit 310 and the collimation unit 320. However, the optical system installed in the optical probe 300 illustrated in FIGS. 6A and 6B differs from the optical system 100 illustrated in FIG. 3 in that the optical system includes a reflecting mirror 350 to change a propagation path of light to be focused. Hereinafter, the optical probe 300 will be described in detail with reference to FIGS. 6A and 6B, and with respect to the optical system of the optical probe 300, it will be described focusing on the differences between the present embodiment and the optical system 100 illustrated in FIG. 3.

Referring to FIGS. 6A and 6B, the optical probe 300 may include a housing 340 to accommodate the optical system therein. The housing 340 may be cylindrical, extending in a length direction (an optical axis direction). The housing 340 may include a proximal end (not illustrated) and a distal end 344, defined on the basis of a location of the light emitting unit 310, and further include a side wall 342 extending between the proximal end and the distal end 344. In addition, the housing 340 may include a transparent window 346 on a portion of the side wall 342 which may be close to the distal end 344, and the transparent window 346 may be provided around the entire circumference (360°) or around a portion of the circumference of the side wall 342. The optical probe 300 may further include a rotation means (not illustrated) to rotate the housing 340 to acquire a 360° image through the transparent window 346 provided on the part of the side wall 342. The rotation means may be one of various types.

The optical system of the optical probe 300 may further include a reflecting mirror 350 to change a propagation path of light traveling from the proximal end to the distal end 344 such that the light is reflected and emitted through the transparent window 346. The reflecting mirror 350 may be in the form of a prism or another optical element as would be understood by one of skill in the art.

Furthermore, the optical system of the optical probe 300 may include a location changing means 352, for example, an actuator, to move the reflecting mirror 350 to change its location. The location changing means 352 may move the reflecting mirror 350 according to a focal length of the focusing lens 330 in order to maintain a constant working distance W. For example, under the assumption that a distance from the transparent window 346 to the object O or the working distance W from an optical axis of the light emitting unit 310 to the object O is fixed, when the focal length of the optical system, more specifically, a focal length of the focusing lens 330 is short in order to acquire a high NA, the location changing means 352 may move the reflecting mirror 350 toward the focusing lens 330 to allow the light to be accurately focused on the object O (refer to FIG. 6A). In contrast, when the focal length of the focusing lens 330 is long in order to acquire a low NA, the location changing means 352 may move the reflecting mirror 350 toward the distal end 334 to allow the light to be accurately focused on the object O (refer to FIG. 6B).

Figure 7A:
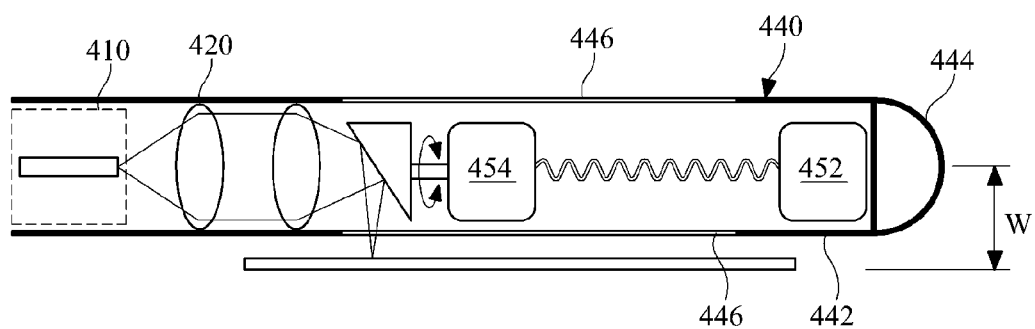
FIG. 7A is a diagram illustrating another optical probe in a given status according to an embodiment.
Figure 7B:
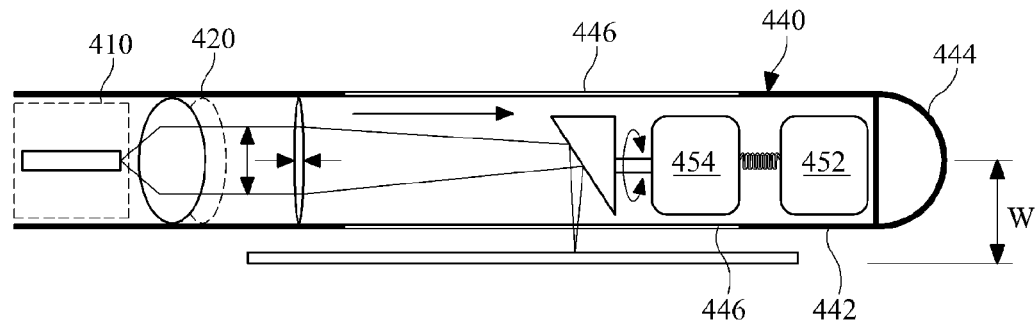
FIG. 7B is a diagram illustrating another optical probe in another given status according to an embodiment.

FIGS. 7A and 7B illustrate a structure of an optical probe 400 according to another embodiment. In the example illustrated in FIG. 7A, the NA of the optical system included in the optical probe 400 is relatively large, and in the example illustrated in FIG. 7B, the NA of an optical system included in the optical probe 400 is relatively small. The optical system of the optical probe 400 shown in FIGS. 7A and 7B may be substantially similar to the optical system 100 shown in FIG. 3. That is, a pupil diameter adjusting means of the optical system shown in FIGS. 7A and 7B is characterized in that a collimation lens 420 is a variable focal lens and a distance adjusting means (not illustrated) is further included to adjust a distance between a light emitting unit 410 and the collimation lens 420. However, the optical system shown in the examples illustrated in FIGS. 7A and 7B is different from the optical system 100 shown in FIG. 3 in that the optical system illustrated in FIGS. 7A and 7B includes a reflecting mirror 450 to change a propagation path of the light to be focused on the optical system. Hereinafter, the optical probe 400 will be described in detail with reference to FIGS. 7A and 7B, and the optical system of the optical probe 400 will be described focusing on the differences between this embodiment and the optical system 100 shown in the example illustrated in FIG. 3.

Referring to FIGS. 7A and 7B, the optical probe 400 may include a housing 440 to accommodate the optical system therein. The housing 440 may be cylindrical, extending in a length direction (an optical axis direction). The housing 440 may include a proximal end and a distal end 444 defined on the basis of a location of a light emitting unit 410, and may further include a side wall 442 extending between the proximal end and the distal end 444. In addition, the housing 440 may include a transparent window 442 on a part of the side wall 442 which may be close to the distal end 444, and the transparent window 442 is provided around the entire circumference (360°) of the side wall 442.

The optical system of the optical probe 400 may further include the reflecting mirror 450 to change a propagation path of light traveling straight from the proximal end of the housing 440 to the distal end and to emit the changed light to the transparent window 446. The reflecting mirror 450 may be in the form of a prism or another optical element as would be understood by one of skill in the art. In this case, the optical probe 400 may further include a rotation means 454 to rotate the mirror 450 440 to acquire an image over 360° through the transparent window 446 provided on the side wall 342 along the entire circumference. The rotation means 454 may be a micro motor, or another device as would be understood by one of skill in the art. The rotation means 454 may be fixed to the reflecting mirror 450.

The optical system of the optical probe 400 may include a location changing means 452, for example, an actuator, to change a location of the reflecting mirror 450. The location changing means 452 may move the reflecting mirror 450 forward and backward according to the focal length of the focusing lens 430, in order to maintain constant a working distance W. In this case, the location changing means 452 may be connected directly and physically to the reflecting mirror 450, or may be physically connected to another element, for example, to the rotation mean 454, that is also fixed to the reflecting mirror 450.

For example, it is assumed that a distance from the transparent window 446 to the object O or the working distance W from an optical axis of the light emitting unit 410 to the object O is fixed. In this case, if a focal length of the focusing lens 430 is short in order to acquire a high NA, the location changing means 452 may move the reflecting mirror 450 toward the focusing lens 430 to allow the light to be accurately focused on the object O (refer to FIG. 7A). In contrast, when the focal length of the focusing lens 430 is long in order to acquire a low NA, the location changing means 452 may move the reflecting mirror 450 toward the distal end 444 to allow the light to be accurately focused on the object O (refer to FIG. 7B).

Figure 8A:
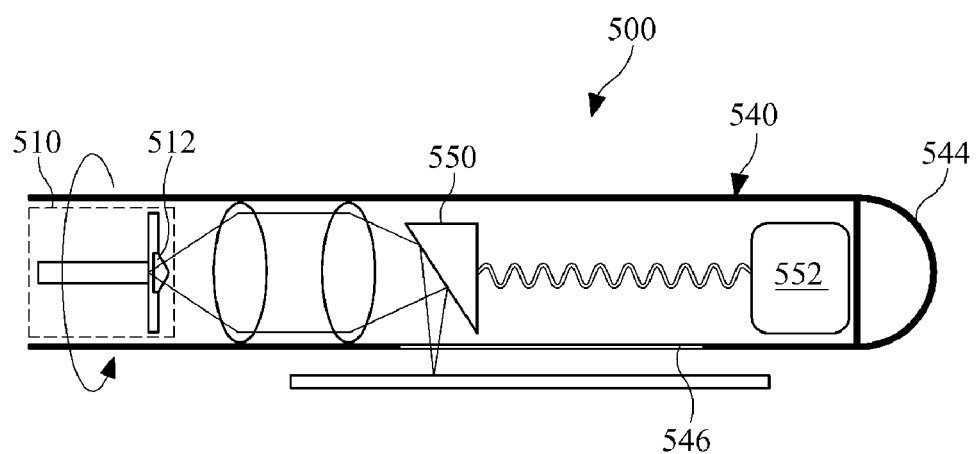
FIG. 8A is a diagram illustrating another optical probe in a given status according to an embodiment.
Figure 8B:
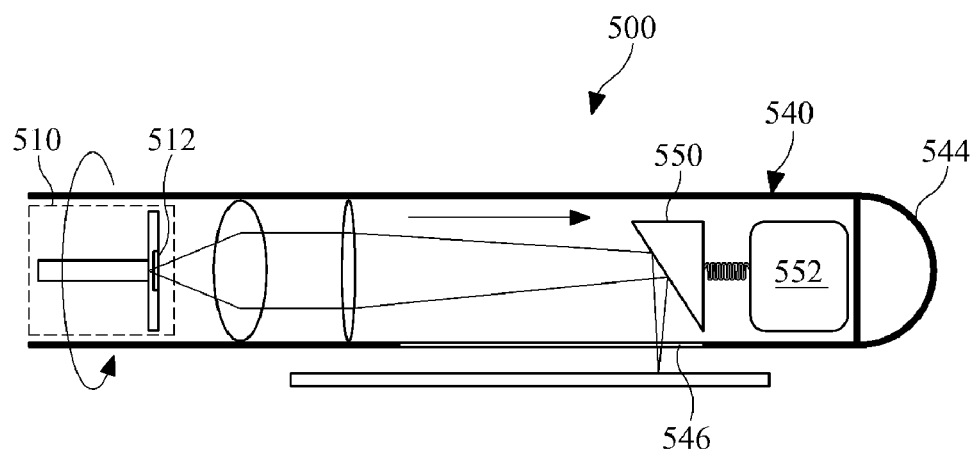
FIG. 8B is a diagram illustrating another optical probe in another given status according to an embodiment.

FIGS. 8A and 8B illustrate an optical probe according to another embodiment. In the example illustrated in FIG. 8A, the NA of the optical system in the optical probe 500 is relatively high, and in the example illustrated in FIG. 8B, the NA of the optical system in the optical probe 500 is relatively large. The optical system in the optical probe 500 shown in the examples illustrated in FIGS. 8A and 8B may be substantially similar to the optical system 200 shown in the example illustrated in FIG. 4. That is, a pupil diameter adjusting means of the optical system included in the optical probe 500 may be a variable focal lens 512 disposed at an end of a light emitting unit 510, and a focal length (i.e., surface form) of the variable focal lens 512 may be changed to adjust the pupil diameter of a collimation lens 520. However, the optical system in the optical probe 500 shown in the examples illustrated in FIGS. 8A and 8B is different from the optical system 200 illustrated in FIG. 4 in that the optical system illustrated in FIGS. 8A and 8B includes a reflecting mirror 550 to change a propagation path of light to be focused on the optical system. Hereinafter, the optical probe 500 shown in the examples illustrated in FIGS. 8A and 8B will be described in detail with reference to FIGS. 8A and 8B, and the optical system of the optical probe 500 will be described focusing on the difference from the optical system 200 illustrated in FIG. 4.

Referring to FIGS. 8A and 8B, the optical probe 500 may include a housing to accommodate the optical system therein. The housing 540 may be cylindrical, extending in a length direction (an optical axis direction). The housing 540 may include a proximal end (not illustrated) and a distal end 544 defined with respect to a location of the light emitting unit 510, and further include a side wall 542 extending between the proximal end and the distal end. In addition, the housing 540 may include a transparent window 546 provided on a side wall 542 close to the distal end 544, and the transparent window 546 may be provided around the entire circumference of the side wall 542 (360°) or may be provided around a part of the circumference of the side wall 542 (refer to FIGS. 7A and 7B). In the latter case, the optical probe 500 may further include a rotation means (not illustrated) to rotate the housing 540 to acquire an image of 360° through the transparent window 546 provided on a part of the side wall 542. The rotation means may be of various types.

The optical system of the optical probe 500 may include the reflecting mirror 550 to change a propagation path of light traveling straight from the proximal end to the distal end 544 such that the light is reflected to be emitted through the transparent window 546. The reflecting mirror 550 may be in the form of prism, or another element as would be understood by one of skill in the art.

The optical system of the optical probe 500 may further include a location changing means 552 to change the location of the reflecting mirror 550, and may include, for example, an actuator. The location changing means 552 may move the reflecting mirror 550 forward and backward according to the focal length of the focusing lens 530 to maintain a constant working distance. For example, it is assumed that a distance from the transparent window 546 to the object O or the working distance W from an optical axis of the light emitting unit 510 to the object O is fixed. In this case, if a focal length of the optical system, or more precisely, the focal length of the focusing lens 530 is short in order to acquire a high NA, the location changing means 552 may move the reflecting mirror 550 toward the focusing lens 530 to allow the light to be accurately focused on the object O (refer to FIG. 8A). In contrast, when the focal length of the focusing lens 530 is long in order to acquire a low NA, the location changing means 552 may move the reflecting mirror 550 toward the distal end 544 to allow the light to be accurately focused on the object O (refer to FIG. 8B).

Figure 9:
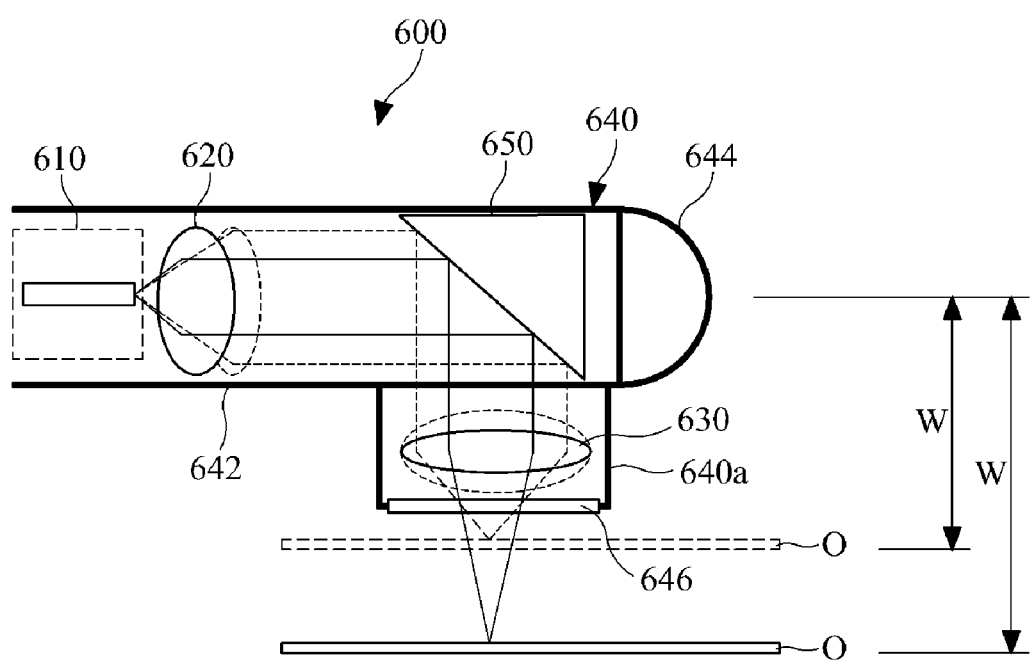
FIG. 9 is a diagram illustrating another optical probe according to an embodiment.

FIG. 9 illustrates a structure of an optical probe according to another embodiment. In the example illustrated in FIG. 9, dotted lines (a focusing lens 630 and an object O) indicate a case in which the NA of the optical system of the optical probe 600 is relatively large, and solid lines (focusing lens 630 and an object O) indicate a case in which the NA is relatively small. The example illustrated in FIG. 9 shows a case in which a working distance W between a light emitting unit 610 and the object O is variable according to a desired NA, while the focusing lens 630 is fixed in its location, and the working distance W may be adjusted by changing a distance between the optical probe 600 and the object O.

In addition, the optical system of the optical probe 600 shown in FIG. 9 may be substantially similar to the optical system 100 shown in the example illustrated in FIG. 3. That is, a pupil diameter adjusting means of the optical system of the optical probe 600 is characterized in that the collimation lens 620 is a variable focal lens and a distance adjusting means (not illustrated) is further provided to adjust a distance between the light emitting unit 610 and the collimation lens 620, and it may be understood by those skilled in the art that the pupil adjusting means included in the optical probe 600 may be identical to the pupil diameter adjusting means of the optical system 200 illustrated in FIG. 4. However, the optical system included in the optical probe 600 is different from the optical system 100 illustrated in FIG. 3 in that the an optical axis of the collimation lens 620 is orthogonal to an optical axis of the focusing lens 630 and the reflecting mirror is provided to change a direction of a propagation path of light transmitted to the focusing lens 630 from the collimation lens 620 to a vertical direction, as shown in FIG. 9. Hereinafter, the optical probe 600 shown in FIG. 9 will be described, and the optical system of the optical probe 600 will be described focusing on the difference between the present embodiment and the optical system 100 illustrated in FIG. 3.

Referring to FIG. 9, the optical probe 600 may include a housing 640 to accommodate the optical system therein. The housing 640 may include a proximal end (not illustrated) and a distal end 644 defined on the basis of a location of the light emitting unit 610, and may further include a side wall 642 extending between the proximal end and the distal end 644. In addition, the housing 640 may be cylindrical, extending in a length direction (an optical axis direction), and may include a protruding portion 640a that protrudes orthogonally from a part of the side wall 642 close to the distal end 644. The protruding portion 640a may have a size and shape sufficient to house the focusing lens 630. Then, an outer surface of the protruding portion 640a may be provided with a transparent window 646.

Moreover, the optical system of the optical probe 600 may further include a reflecting mirror 650 to change the propagation path of light traveling straight from the proximal end to the distal end 644 to reflect the light and emit the reflected light toward the lens 630 and through the transparent window 646. The reflecting mirror 650 may be in the form of prism or another element as would be understood by one of skill in the art. However, the optical system of the optical probe 600 may omit a location changing means to change a location of the reflecting mirror 650. The optical probe 600 may adjust a distance between the transparent window 646 and the object O to correspond to a focal length of the focusing lens 630 according to a value of the desired NA.

Figure 10:
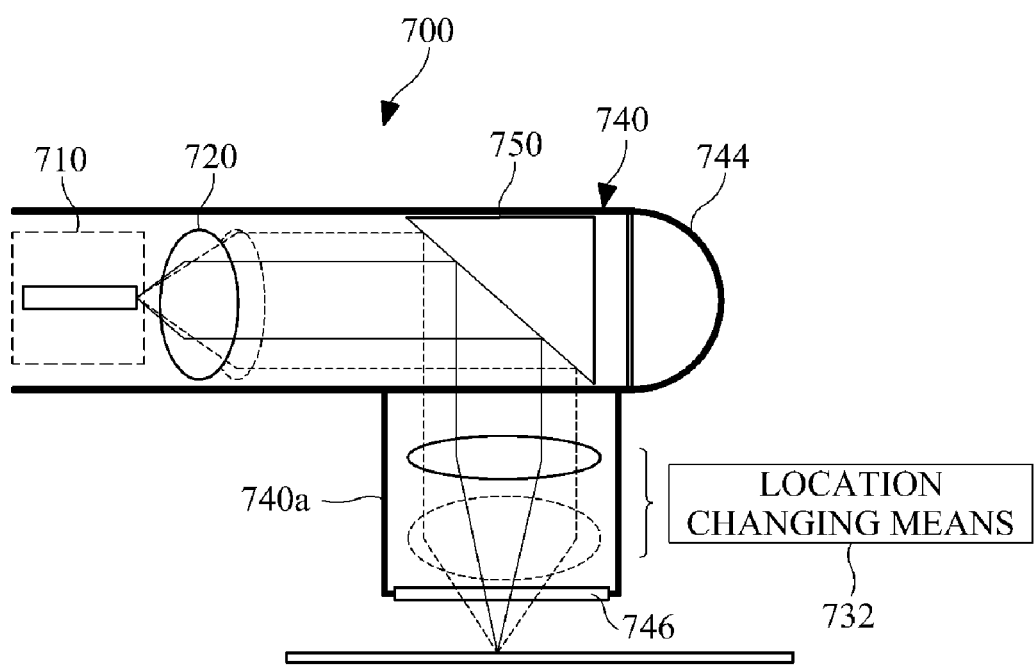
FIG. 10 is a diagram illustrating another optical probe according to an embodiment.

FIG. 10 illustrates a structure of an optical probe according to another embodiment. In the example illustrated in FIG. 10, dotted lines (the focusing lens 730 and the object O) indicate a case in which the NA of the optical system of the optical probe 700 is relatively large, and solid lines (focusing lens 730 and the object O) indicate a case in which the NA is relatively small. The example illustrated in FIG. 10 shows a case in which the focusing lens 730 is moved to change its location according to a desired NA while a distance between the optical probe 700 and the object O is fixed.

In addition, the optical system of the optical probe 700 shown in FIG. 10 may be substantially similar to the optical system 100 shown in the example illustrated in FIG. 3. That is, a pupil diameter adjusting means of the optical system of the optical probe 700 is characterized in that a collimation lens 720 is a variable focal lens and a distance adjusting means (not illustrated) is further provided to adjust a distance between the light emitting unit 710 and the collimation lens 720, and it may be understood by those skilled in the art that the pupil adjusting means included in the optical probe 700 may be the same as the pupil diameter adjusting means of the optical system 200 illustrated in FIG. 4. In addition, the optical system of the optical probe 700 may further include a location changing means (not illustrated) to change a location of the focusing lens 730, and the location changing means may be the same as the location changing means 332 of the optical system 100 illustrated in FIG. 3.

However, the optical system included in the optical probe 700 is different from the optical system 100 illustrated in FIG. 3 in that the an optical axis of the collimation lens 720 is orthogonal to the optical axis of the focusing lens 730 and the reflecting mirror is provided to change a direction of a propagation path of light transmitted to the focusing lens 730 from the collimation lens 720 to an orthogonal direction such that the light is reflected towards the focusing lens 730. Hereinafter, the optical probe 700 shown in the example illustrated in FIG. 10 will be described, and the optical system of the optical probe 700 will be described focusing on the differences between the present embodiment and the optical system 100 illustrated in FIG. 3.

Referring to FIG. 10, the optical probe 700 may include a housing 740 to accommodate the optical system therein. The housing 740 may include a proximal end (not illustrated) and a distal end 744 defined on the basis of a location of the light emitting unit 710, and may further include a side wall 742 extending between the proximal end and the distal end 744. In addition, the housing 740 may be cylindrical, extending in a length direction (an optical axis direction of the collimation lens 720), and may include a protruding portion 740a that protrudes orthogonally from a part of the side wall 742 close to the distal end 744. The protruding portion 740a may have a size sufficient to house the focusing lens 730 and allow the focusing lens 730 to move within the protruding portion 740a. In addition, the protruding portion 740a may have an outer surface provided with a transparent window 746.

Furthermore, the optical system of the optical probe 700 may further include a reflecting mirror 750 to change the propagation path of light traveling straight from the proximal end to the distal end 744 and reflect the light to be transmitted to the focusing lens 740a and through the transparent window 746. The reflecting mirror 750 may be in the form of prism or another element as would be understood by one of skill in the art. However, the optical system of the optical probe 700 may omit a location changing means to change a location of the reflecting mirror 750. The optical probe 700 may adjust a distance between the focusing lens 730 and the object O to correspond to a focal length of the focusing lens 730 according to a desired value of the NA. To this end, the optical probe 700 may further include a location changing means 732 to change a location of the focusing lens 730. The location changing means 732 may be of various types.

Exemplary embodiments have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An optical system comprising:
a light emitting unit comprising a light source;
a collimation lens which collimates light emitted from the light emitting unit;
a pupil diameter adjusting means for adjusting a pupil diameter of the collimation lens; and
a focusing lens which focuses light transmitted from the collimation lens onto an object;
a first reflecting mirror which reflects light emitted from the collimation lens and emits the reflected light to the focusing lens; and
a location changing means for changing a location of the focusing lens,
wherein a focal length of the focusing lens is variable, and
wherein an optical axis of the collimation lens is orthogonal to an optical axis of the focusing lens.

2. The optical system of claim 1, wherein:
the pupil diameter adjusting means comprises a distance adjusting means for changing a distance between the light emitting unit and the collimation lens, and
the collimation lens comprises a variable focus lens having a variable focal length.

3. The optical system of claim 1, wherein the pupil diameter adjusting means comprises a variable focal lens which is disposed at an end of the light emitting unit from which the light is emitted and which refracts light incident thereon, thereby changing an angle by which the light is emitted by the light emitting unit.

4. The optical system of claim 1,
wherein the focusing lens comprises a variable focal lens.

5. The optical system of claim 1, further comprising:
a second reflecting mirror which reflects light emitted from the focusing lens and transmits the reflected light to the object.

6. The optical system of claim 5, further comprising:
a distance adjusting means for changing a distance between the focusing lens and the second reflecting mirror.

7. An optical probe comprising:
a housing comprising at least one side wall and a transparent window in the at least one sidewall; and
an optical system disposed within the housing, the optical system comprising a collimation lens and a focusing lens;
a first reflecting mirror which reflects light emitted from the collimation lens and emits the reflected light to the focusing lens; and
a location changing means for changing a location of the focusing lens with respect to the reflecting mirror,
wherein a pupil diameter of the collimation lens is adjustable and a focal length of the focusing lens is adjustable, and thereby a numerical aperture of the optical system is adjustable, and
wherein an optical axis of the collimation lens is orthogonal to an optical axis of the focusing lens.

8. The optical probe of claim 7, wherein the optical system further comprises:
a light emitting unit which comprises a light source, and
a pupil diameter adjusting means of adjusting the pupil diameter of the collimation lens,
wherein the collimation lens collimates the light emitted from the light emitting unit, and the focusing lens focuses the light transmitted from the collimation lens.

9. The optical probe of claim 8, wherein
the focusing lens comprises a variable focal lens.

10. The optical probe of claim 8, wherein the optical system further comprises a second reflecting mirror which reflects light emitted from the focusing lens and which emits the reflected changed light to the transparent window.

11. The optical probe of claim 10, further comprising:
a distance adjusting means of changing a distance between the focusing lens and the second reflecting mirror.

12. An optical probe comprising:
a housing comprising at least one side wall and a transparent window in the at least one sidewall; and
an optical system disposed within the housing, the optical system comprising a collimation lens and a focusing lens,
wherein a pupil diameter of the collimation lens is adjustable and a focal length of the focusing lens is adjustable, and thereby, a numerical aperture of the optical system is adjustable,
wherein the optical system further comprises:
light emitting unit which comprises a light source;
a pupil diameter adjusting means of adjusting the pupil diameter of the collimation lens; and
a reflecting mirror which reflects light emitted from the focusing lens and which emits the reflected light to the transparent window,
wherein the collimation lens collimates the light emitted from the light emitting unit, and the focusing lens focuses the light transmitted from the collimation lens,
wherein the optical probe further comprises a rotation means for rotating the reflecting mirror, and
wherein the at least one side wall is cylindrical and the transparent window is provided around an entire circumference of the side wall.

13. The optical probe of claim 10, further comprising:
a rotation means for rotating the housing with respect to at least one element of the optical system.

14. An optical probe comprising:
a housing having a transparent window therein; and
an optical system comprising:
a light source which provides divergent light,
a collimation lens which collimates light provided by the light source;
a focusing lens which focuses light emitted from the collimation lens;
a numerical aperture adjusting means for adjusting a numerical aperture of the optical system;
a first reflecting mirror which reflects light emitted from the collimation lens and emits the reflected light to the focusing lens; and
a location changing means for changing a location of the focusing lens with respect to the reflecting mirror,
wherein an optical axis of the collimation lens is orthogonal to an optical axis of the focusing lens, and
wherein the numerical aperture adjusting means comprises a pupil diameter adjusting means for adjusting a pupil diameter of the collimation lens, and a focal length adjusting means for adjusting a focal length of the focusing lens.

15. The optical probe of claim 14, wherein
the pupil diameter adjusting means comprises one of a variable focal lens disposed between the light source and the collimation lens and a distance adjusting means for changing a distance between the light source and the collimation lens.

16. The optical probe of claim 14, wherein the focusing lens is a variable focal lens.

17. The optical probe of claim 15, wherein the focusing lens is a variable focal lens.

18. The optical probe of claim 14, wherein the optical system further comprises a second reflecting mirror which reflects light from the focal lens to the transparent window.

19. An optical system comprising:
a light emitting unit comprising a light source;
a collimation lens which collimates light emitted from the light emitting unit;
a pupil diameter adjusting means for adjusting a pupil diameter of the collimation lens;
a focusing lens which focuses light transmitted from the collimation lens onto an object;
a first reflecting mirror which reflects light emitted from the collimation lens and emits the reflected light to the focusing lens; and
a location changing means for changing a location of the focusing lens,
wherein a focal length of the focusing lens is variable.

20. An optical system comprising:
a light emitting unit comprising a light source;
a collimation lens which collimates light emitted form the light emitting unit;
a focusing lens which focuses light transmitted form the collimation lens onto an object; a numerical aperture adjusting means for adjusting a numerical aperture of the optical system;
a first reflecting mirror which reflects light emitted from the collimation lens and emits the reflected light to the focusing lens;
wherein a focal length of the focusing lens is variable, and wherein an optical axis of the collimation lens is orthogonal to an optical axis of the focusing lens; wherein the numerical aperture adjusting means comprises a pupil diameter adjusting means for adjusting a pupil diameter of the collimation lens, and a focal length adjusting means for adjusting a focal length of the focusing lens.

* * * * *